United States Patent
Acquista

(10) Patent No.: US 7,979,111 B2
(45) Date of Patent: Jul. 12, 2011

(54) WIRELESS ELECTRODE ARRANGEMENT AND METHOD FOR PATIENT MONITORING VIA ELECTROCARDIOGRAPHY

(76) Inventor: Angelo Joseph Acquista, New York, NY (US)

(*) Notice: Subject to any disclaimer, the term of this patent is extended or adjusted under 35 U.S.C. 154(b) by 843 days.

(21) Appl. No.: 11/454,374

(22) Filed: Jun. 15, 2006

(65) Prior Publication Data
US 2007/0293774 A1    Dec. 20, 2007

(51) Int. Cl.
*A61B 5/0402* (2006.01)
(52) U.S. Cl. .................................................. 600/509
(58) Field of Classification Search .................... 600/509
See application file for complete search history.

(56) References Cited

U.S. PATENT DOCUMENTS

| | | | |
|---|---|---|---|
| 4,850,370 A | 7/1989 | Dower | |
| 6,052,615 A | 4/2000 | Feild et al. | |
| 6,217,525 B1 | 4/2001 | Medema et al. | |
| 6,405,083 B1 | 6/2002 | Rockwell et al. | |
| 6,416,471 B1* | 7/2002 | Kumar et al. | 600/300 |
| 6,611,705 B2 | 8/2003 | Hopman et al. | 600/509 |
| 6,643,539 B2 | 11/2003 | Meij et al. | |
| 6,740,033 B1* | 5/2004 | Olejniczak et al. | 600/301 |
| 6,773,396 B2 | 8/2004 | Flach et al. | |
| 6,829,501 B2 | 12/2004 | Nielsen et al. | |
| 6,976,965 B2 | 12/2005 | Corl et al. | |
| 7,004,907 B2 | 2/2006 | Banet et al. | |
| 7,197,357 B2 | 3/2007 | Istvan et al. | 600/509 |
| 7,272,428 B2 | 9/2007 | Hopman et al. | 600/382 |
| 7,387,607 B2* | 6/2008 | Holt et al. | 600/301 |
| 7,403,808 B2 | 7/2008 | Istvan et al. | 600/393 |
| 2004/0015058 A1* | 1/2004 | Besson et al. | 600/301 |
| 2004/0112964 A1* | 6/2004 | Empedocles et al. | 235/491 |
| 2005/0017864 A1 | 1/2005 | Tsoukalis | |
| 2005/0054941 A1* | 3/2005 | Ting et al. | 600/529 |
| 2005/0102026 A1* | 5/2005 | Turner et al. | 623/2.1 |
| 2005/0119701 A1 | 6/2005 | Lauter et al. | |
| 2005/0215916 A1* | 9/2005 | Fadem et al. | 600/544 |
| 2006/0084855 A1 | 4/2006 | Teschner et al. | |

FOREIGN PATENT DOCUMENTS

WO    98/41279    9/1998

OTHER PUBLICATIONS

Fulford-Jones et al. "A Portable, low-Power, Wireless Two Lead EKG System." Proceedings of the 26th Annual International Conference of the IEEE EMBS, Sep. 1, 2005, pp. 2141-2144.*

Thomas Hoffman, "Smart Dust—Mighty motes for medicine, manufacturing, the military", www.computerworld.com, Mar. 24, 2003.

(Continued)

*Primary Examiner* — Eric D. Bertram
(74) *Attorney, Agent, or Firm* — Stroock & Stroock & Lavan LLP

(57) ABSTRACT

A wireless electrocardiogram (ECG) system is disclosed. The wireless ECG provides for recording potentials on the surface of a body. The wireless ECG includes a plurality of electrodes suitable for attachment to the surface of the body, a voltage measuring circuit for detecting a voltage between a reference voltage level and electrodes, an error detecting circuit, and a transmitting circuit for transmitting the detected voltage signal to a receiver. The disclosed system is robust in that it provides the capability of continuous monitoring of a subject while correcting for defects in an electrode, contact, presence of excessive noise or other developments in addition to providing the customary alarms in the event of disruptions.

23 Claims, 10 Drawing Sheets

OTHER PUBLICATIONS

Michael Singer, "Smart Dust Collecting in the Enterprise", www.internetNewsBureau.com, Oct. 24, 2003.

Gordon E. Dower, M.D., "The ECGD: A Derivation of the ECG from VCG Leads", J.Electrocardiology 17 (2), 1984, 189-192.

Dower et al., "XYZ Data Interpreted by a 12-Lead Computer Program using the Derived Electrocardiogram", J. Electrocardiology 12 (3), 1979, 249-261.

He et al., "Body Surface Laplacian ECG Mapping", IEEE Transactions on Biomedical Engineering, vol. 39, No. 11, Nov. 1992, 1179-1191.

* cited by examiner

WIRELESS ELECTRODE ARRANGEMENT AND METHOD FOR PATIENT MONITORING VIA ELECTROCARDIOGRAPHY

FIELD OF THE INVENTION

The present invention relates to a novel wireless cardiographic monitoring. More particularly, the present invention relates to an improved wireless cardiographic monitoring with low power requirements and providing comfort while continually monitoring cardiac activity, temperature, hemodynamic parameters and storing personal statistics.

BACKGROUND OF THE INVENTION

An electrocardiogram (ECG) measurement is conventionally performed using a 12-lead system, although formats with alternative number of leads are also known. The production of a conventional 12-lead electrocardiogram (ECG) involves the placement of about 10 electrodes or less (one of which is a ground or reference electrode) at selected points on the surface of a subject's body. Each electrode acts in combination with one or more other electrodes to detect voltages produced by depolarization and repolarization of individual heart muscle cells. The detected voltages are combined and processed to produce 12 tracings of time varying voltages. The tracings so produced are as follows:

| Lead | Voltage | Lead | Voltage |
| --- | --- | --- | --- |
| I | vL − vR | V1 | v1 − (vR + vL + vF)/3 |
| II | vF − vR | V2 | v2 − (vR + vL + vF)/3 |
| III | vF − vL | V3 | v3 − (vR + vL + vF)/3 |
| aVR | vR − (vL + vF)/2 | V4 | v4 − (vR + vL + vF)/3 |
| aVL | vL − (vR + vF)/2 | V5 | v5 − (vR + vL + vF)/3 |
| aVF | vF − (vL + vR)/2 | V6 | v6 − (vR + vL + vF)/3 | where, in the standard, most widely used system for making short term electrocardiographic recordings of supine subjects, the potentials indicated above, and their associated electrode positions, are:
  vL potential of an electrode on the left arm;
  vR potential of an electrode on the right arm;
  vF potential of an electrode on the left leg;
  v1 potential of an electrode on the front chest, right of sternum in the 4th rib interspace;
  v2 potential of an electrode on the front chest, left of sternum in the 4th rib interspace;
  v4 potential of an electrode at the left mid-clavicular line in the 5th rib interspace;
  v3 potential of an electrode midway between the v2 and v4 electrodes;
  v6 potential of an electrode at the left mid-axillary line in the 5th rib interspace;
  v5 potential of an electrode midway between the v4 and v6 electrodes;
  vG (not indicated in table above) is a ground or reference potential with respect to which potentials vL, vR, vF, and v1 through v6 are measured. Typically, though not necessarily, the ground or reference electrode is positioned on the right leg.

Correct interpretation of an ECG requires a great deal of experience since it involves familiarity with a wide range of patterns in the tracings of the various leads.

Other lead systems have evolved from improvements in instrumentation that have permitted extension of electrocardiography to ambulatory, and even vigorously exercising subjects, and to recordings made over hours, or even days. For example, in stress testing the electrodes are moved from the arms to the trunk, although the same number of electrodes (10) may be used. The tracings I, II, III, aVR, aVL and aVF are altered by this modification.

Although a 12-lead ECG is considered to be a cost effective heart test, it is to be noted that the requirement for a relatively large number of electrodes plays an important role in determining patient convenience/comfort, costs, such as the cost of the electrodes themselves, and the time required to properly position and fix each electrode to a subject's body.

Multiple formats or lead systems reflect the fact that signals representing the respective lead signals typically contain mutually redundant information. It is also known that, should one electrode be missing or malfunctioning, an appropriate combination of signals from the other electrodes and/or the other leads, if available and functional, can be used to generate a synthesized signal to approximate the lead signal derived from the missing or malfunctioning electrode. To apply this technique, at least some portion of a full 12-lead ECG is recorded, during an analysis phase. The recorded signals are then processed to generate a function, preferably a linear function, which may be applied to the lead signals which are available to synthesize a lead signal that approximates the lead signal that is missing or distorted beyond use. During a synthesis phase, this function is then applied to the available ECG lead signals. Using this technique, a missing lead may be synthesized. For example, U.S. Pat. No. 6,643,539 discloses a method of generating a set of synthesized ECG lead signals from a subset of ECG lead signals using synthesis matrices. The method involves creating a synthesis transform matrix relating the signals from an electrode subset to the signals from the conventional 12-leads for different electrode subset configurations of one or more missing electrodes. If ECG signals are taken with one or more missing electrodes, then appropriate synthesis matrix transform is applied to recover the full 12-lead ECG signals.

Efforts have also been made to reduce the number of electrodes needed to collect the ECG signals in order to reduce costs (e.g., of the electrodes), complexity and the time required for electrode positioning. The Dower "EASI" lead system provides a method for sensing and analyzing activity of the human heart that requires use of a reduced number of electrodes to produce accurate simulations of conventional 12-lead electrocardiograms (see, e.g., U.S. Pat. No. 4,850, 370). The A and I electrodes (the second and third electrodes) are placed on opposite sides of the anterior midline of the subject at the same level as the first electrode (the E electrode), while electrode S is positioned over the upper end of the sternum (manubrium sterni). However, over the years it has been noted that the signal coming from the A-I electrode pair often contains a higher than desirable level of electrical artifact, probably generated by the nearby pectoral muscles.

To address this problem, U.S. Pat. No. 6,052,615 discloses a modified "EASI" method where the 4 electrode positions consist of electrode E positioned at the front midline, modified electrode A positioned at the left mid-axillary line, electrode S positioned over the upper end of the sternum (manubrium sterni), and modified electrode I positioned at the right mid-axillary line. (Such E, A, S and I electrodes are from time-to-time collectively referred to herein as the "EASI" electrodes.) Specifically, the modified A and I electrodes are attached to the subject's is body on opposed sides of the anterior midline below the level of the E electrode but high enough so they are positioned over the subjects' ribs or intercostal spaces.

Given the greater mobility with the reduced number of electrodes, methods and systems have also been developed for monitoring a subject's medical condition using ECG signals. For example, U.S. Pat. No. 6,217,525 discloses a method and device that evaluates the electrical activity of a patient's heart using a reduced set of leads to automatically detect and report abnormalities associated with acute cardiac ischemia. The reduced set of leads are derived from ECG data obtained from a reduced number of electrodes (i.e., fewer than ten electrodes as used in a conventional 12-lead ECG system) placed on a patient. Cardiac ischemia is detected based on prior classifications of local features and/or global features of the ECG data. Local features include well known local morphological measures such as ST elevation, T wave amplitude, and QRS area from the ECG data, and clinical information on the patient such as age and sex. Global features include projection coefficients calculated from projecting a concatenated vector of heartbeat data onto separate sets of basis vectors that define signal subspaces of ischemic and non-ischemic ECGs. One or more classifiers evaluate the local features and/or global features to determine whether an acute cardiac ischemic condition is detected.

Attempts have also been made to develop medical telemetry systems to improve a patient's comfort, freedom and privacy by decreasing the number and volume of devices directly or indirectly attached to the patient. Telemetry systems normally comprise a transmitter for transmitting electromagnetic signals, e.g., from a measurement, and a receiver for receiving the electromagnetic signals from the transmitter. The ECG electrodes attached to the patient lead to the transmitter, which is usually carried by the patient. The receiver is typically installed in an operator room. Large systems may have a multitude of transmitters and receivers, such as disclosed in U.S. Pat. No. 6,773,396. Each transmitter normally operates with a corresponding receiver on a certain channel, preferably over a pre-defined carrier frequency. Most telemetry systems are single-parameter telemetry systems, whereby a complete telemetry system comprising sensor and transmitter is required for each parameter to be monitored. U.S. Pat. No. 6,740,033 discloses a multi-parameter wireless telemetry system for medical purposes. In another example, U.S. Pat. No. 6,829,501 discloses a system where the electrodes connected to the patient are in communication with a patient monitor console through a telemetry-based transmitter transmitting a radio frequency ("RF") signal to one or more antennas connected to the patient monitor console through a conventional RF receiver.

United States Patent Publication No. 2005/0017864 discloses a system which also uses wireless communication. However, the system utilizes circular concentric circuit detector electrodes, which are described as Laplacian electrodes. The signals from the electrodes are processed to detect alarm conditions, such as arrhythmia types. In particular, it should be noted that the Laplacian electrodes do not provide a measure of the voltage at the electrode contact point. Rather, the output of the Laplacian electrodes provides a measure of the two-dimensional Laplacian of the potential (which is proportional to the charge density at the center point of the Laplacian electrode). See, e.g., Bin He and Richard J. Cohen, *IEEE Transactions on Biomedical Engineering*, vol. 39, no. 11, pp. 1179-1191 (November 1992).

As a result, there remains a need for an ECG system that improves patient comfort and freedom of motion by decreasing wired devices attached to the patient to allow for greater freedom while being worn even all the time. There is also a need for a system that monitors the patient's conditions, and provides an alarm in the event of an alarm condition (e.g., ischemia). There is also a need for a system that reduces the power and bandwidth requirements for monitoring a patient. There is also a need for flexible monitoring of a patient to respond to different contexts. Furthermore, there is a need for a systems that includes an error detecting and correcting functionality to detect an error in the measurement, e.g., if an electrode falls off the patient's body, and to select one or more replacement electrodes.

SUMMARY OF THE INVENTION

The present invention provides a system for recording potentials on the surface of a subject's body. The system preferably includes a plurality of electrodes suitable for attachment to the surface of the body, where each electrode is attached to the surface by means of an attachment end of the electrode. The system detects a voltage signal via wireless transmissions from the electrodes using a voltage measuring circuit. In preferred embodiments, the system detects a voltage relative to a reference voltage level. The system preferably includes an error detecting circuit for detecting errors in the voltage signal from the electrodes. The electrodes are preferably provided with or connected to a transmitting circuit for transmitting a detected voltage signal. Signal transmissions preferably use low power and use bandwidth flexibly. Notably, the error detecting circuit may also or instead be provided at the electrodes.

Because the 12 lead ECG is but one format in which data may be presented, it is possible to separate the task of measuring voltages using electrodes in contact with a patient and then generating ECG potentials corresponding to a specified number of electrodes. In effect, the generation task is that of formatting the collected data in a desired form.

In a preferred embodiment, a plurality of electrodes capable of transmitting their measurements over a wireless link are attached to a patient's body. The wireless transmissions are received and correlated with the recorded potentials in a calibration step. The calibration step determines the parameters for deducing data significant for electrocardiograms from the various voltages recorded from the electrodes. It should be noted that not all of the electrodes need be used. Instead a subset of the electrodes are used. In the event improvement in the data is desired or the data are compromised due to failure of one or more electrodes, corrective electrodes are selected to supplement or replace the defective electrodes.

These and other features of the claimed invention are further described with the assistance of the following illustrative drawings and the detailed description.

BRIEF DESCRIPTION OF THE DRAWINGS

The present invention can be better understood by reference to the following drawings, wherein like references numerals represent like elements. The drawings are merely exemplary and the present invention is not limited to the embodiments shown.

DETAILED DESCRIPTION OF THE INVENTION

The present invention addresses the need for a wireless ECG system that is small and portable, hence increasing user comfort, so that it can be worn at all time. The system disclosed herein also provides for monitoring a patient's medical condition through the ECG signals, and providing an alarm in the event that an alarm medical condition is detected, such as ischemia. The system also provides an alarm is an error in the ECG signal is detected, e.g., if an electrode falls off or malfunctions.

The system disclosed herein provides for recording potentials on the surface of a subject's body. The system includes a plurality of electrodes suitable for attachment to the surface of the body, where each electrode is attached to the surface by means of an attachment end of the electrode. In other embodiments, each electrode has two ends, one of which is an attachment end such that the attachment end detects only one voltage signal on the surface at a time, and the second attachment end is the reference voltage level.

The system detects a voltage signal from the electrodes using a voltage measuring circuit. In preferred embodiments, the system detects a voltage between a reference voltage level and the attachment end of the electrode. The system further includes an error detecting circuit for detecting errors in the voltage signal from the electrodes, and a transmitting circuit for transmitting a detected voltage signal to a receiver.

In specific embodiments, the system includes a power supply having one or more of a battery, a transducer for providing electrical potential, and a receiver powered by external power. Also, the system may further include a circuit printed on a flexible surface.

Figure 1:
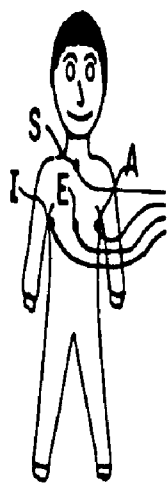
FIG. 1 shows the Dower "EASI" lead system.
Figure 2:
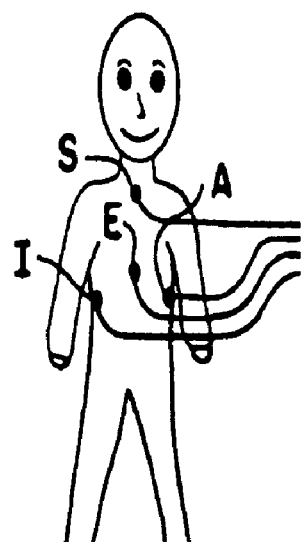
FIG. 2 shows the modified "EASI" lead system.

The present invention is applicable to any number or configuration of electrodes known in the art. FIGS. 1 to 4 illustrate different electrode placement configurations that have been disclosed in the art. FIG. 1 shows the Dower "EASI" lead system disclosed in U.S. Pat. No. 4,850,370, where the A and I electrodes (the second and third electrodes) are placed on opposite sides of the anterior midline of the subject at the same level as the first electrode (the E electrode), while electrode S is positioned over the upper end of the sternum (manubrium sterni). FIG. 2 shows the modified "EASI" lead system disclosed in U.S. Pat. No. 6,052,615, where electrode E is positioned at the front midline, modified electrode A is positioned at the left mid-axillary line, electrode S is positioned over the upper end of the sternum (manubrium sterni), and modified electrode I is positioned at the right mid-axillary line. In particular, the modified A and I electrodes are attached to the subject's is body on opposed sides of the anterior midline below the level of the E electrode but high enough so they are positioned over the subjects' ribs or intercostal spaces.

Figure 3:
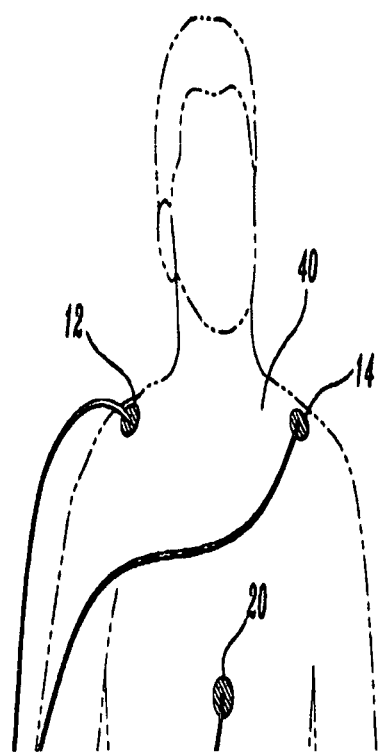
FIG. 3 illustrates yet another example of a system using a reduced number of leads.
Figure 4:
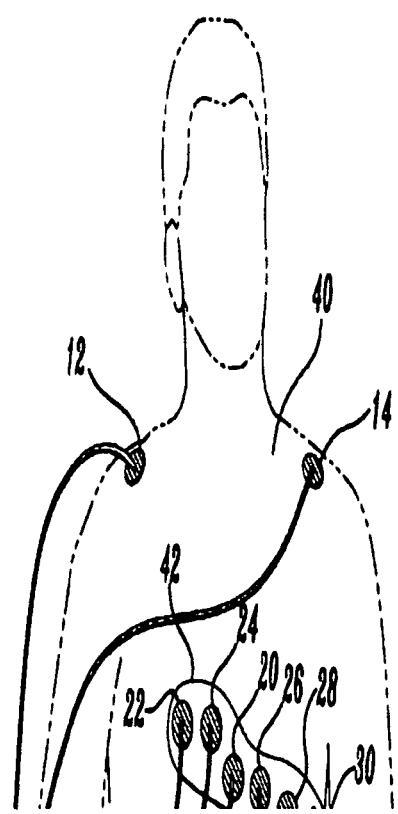
FIG. 4 illustrates a standard positions for a 12-lead ECG configuration.

FIG. 3 illustrates yet another example of a system using a reduced number of leads attached to a patient 40 via electrodes 12, 14, 16, 18, and 20. The five electrodes are attached to the skin of the patient at a variety of locations. The first and second electrodes 12 and 14 are shown attached to the right and left shoulder areas of the patient 40. The third and fourth electrode 16 and 18 are shown attached to the left and right side areas of the patient's torso near the patient's legs. A fifth sensing electrode 20 is shown attached to the patient's chest area over the heart. FIG. 3 also illustrates yet another electrode configuration. In particular, electrodes 12, 14, 16, and 18 may be placed at the ends of the limbs of the patient 40 as indicated by the open circles 42, 44, 46, and 48, respectively. Electrodes 12, 14, 16, and 18 may also be placed at other locations on the patient's torso.

The signals received from the electrodes configurations described above are used to produce ECG data in a manner well-known to those skilled in 12-lead ECG technology. Since the techniques for producing ECG lead data are well-known, a procedure for producing ECG lead data is not described here. Also, techniques for extracting information on the patient's condition from the voltage signals, including diagnoses of ischemia, are well-known and are not described here.

The different electrode configurations permit an analysis of a subset of the leads normally acquired in a standard 12-lead ECG, including the leads conventionally labeled I, II, III, V3, aVR, aVL, and aVF. For example, with the configuration of FIG. 3, one can obtain and analyze leads I, II, and V3. It should be appreciated, however, that other leads, e.g., leads conventionally labeled III, aVR, aVF, aVL, V1, V2, V4, V5, and V6, may be selected and made available in other embodiments of the invention depending on the number and placement of electrodes used.

Those skilled in ECG technology will appreciate that increasing the number of electrodes placed on the patient 40 increases the amount of ECG data that can be acquired from the patient. The additional ECG data obtained from an increased number of electrodes generally improves the ability of the system to detect true acute cardiac ischemic conditions. The reduced electrode configurations described above may be compared to the standard positions for a 12-lead ECG configuration illustrated in FIG. 4, including electrodes 12, 14, 16, 18, 20, 22, 24, 26, 28 and 30. The electrodes may be individually attached to a patient's chest, or embodied in a single patch 42 that is placed on the patient's chest.

Figure 5:
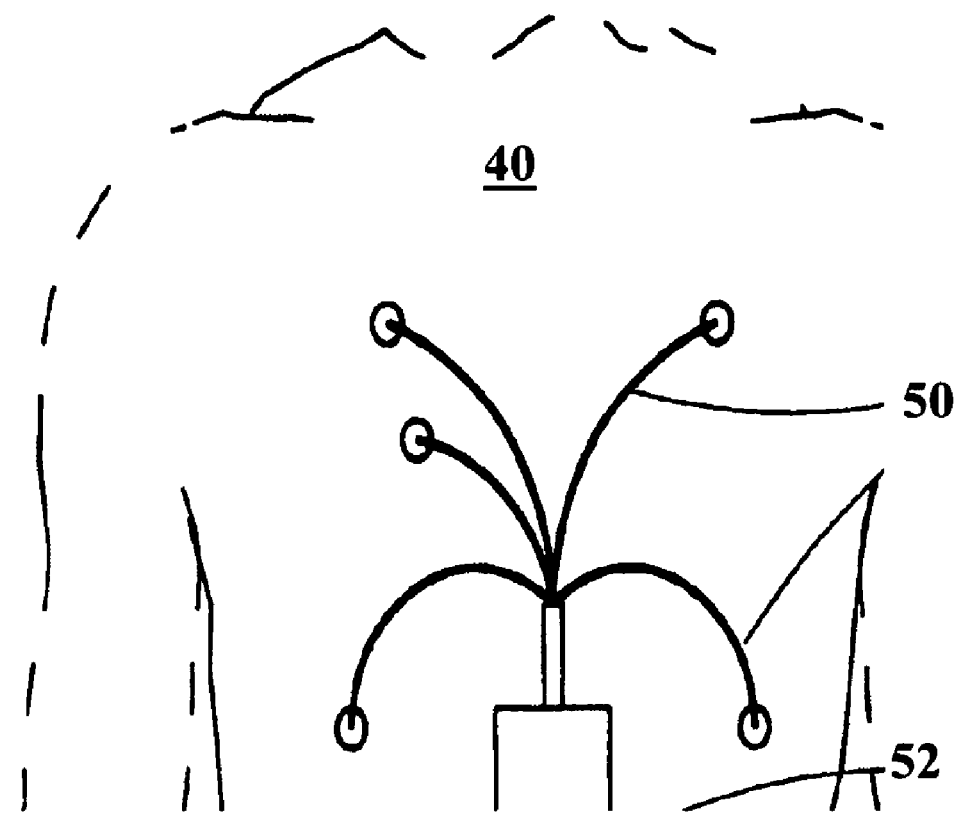
FIG. 5 shows the electrodes attached to the patient and attached by leads to a remote telemeter.

In different embodiments of the instant invention, the voltage signal from the electrodes is transmitted or transferred to a receiver by a transmitting circuit over a wireless medium. In an exemplary embodiment illustrated in FIG. 5, the electrodes 50 attached to the patient 40 may be attached by leads to Remote Telemeter 52. In specific embodiments, Remote Telemeter 52 includes a transmitting circuit. Remote telemeter 52 may include patient-worn or transported remote telemeters, and instrument remote telemeters (which connect to a bedside or other patient monitor). Remote Telemeter 52 collects and transmits real-time ECG voltage signals from Patient 40 to a receiver. Remote Telemeter 52 may further include an error detecting circuit for detecting errors in the voltage signal from any of the electrodes, such as if an electrode comes loose. The details of error detection, including by the preferred method of analysis-by-synthesis, which uses estimates error between a predicted signal and the actual signal, are described later in this disclosure. At this stage, it suffices to note that remote telemeter is connected to or contains processing capability to reduce the bandwidth required to transmit the measured voltage signals by transmitting parameters used to predict the voltage measurements and/or indicators of the error signal. The error signal indicators are selected to minimize the error between the transmitted error information and the detected error information. This feature allows both a reduction in the required bandwidth and added flexibility such that the level of detail transmitted to a receiver corresponds to the expected application or monitoring.

Remote Telemeter 52 sends a corresponding signal to the receiver. In the event that the system detects an alarm medical condition, such as ischemia, or too few electrodes, then the system would send an alarm to alert the pertinent medical professionals of the patient's condition. In different embodiments, Remote Telemeter 52 or the receiver may send the alarm concerning the patient's condition.

In another embodiment of the invention, the electrodes include the transmitting circuit and the error detecting circuit. The electrodes would then not be connected by leads to a remote telemeter as in previous examples. The voltage signal collected by the electrode would be directly transmitted or transferred to the receiver by the transmitting circuit. In particular, if one of the electrodes comes loose, then the electrode would send a corresponding signal to the receiver, including, for instance by a failure to send a signal in an expected time window. The system would send an alarm to alert the pertinent medical professionals in the event of an alarm medical condition or if too few electrodes are available to synthesize the ECG electrodes. In different embodiments, the loose electrode itself or the receiver sends the signal to the medical professionals.

The system of the present invention includes a voltage measuring circuit for detecting a voltage between a reference voltage level and at least one of the electrodes. Alternatively, the voltage measuring circuit may detects voltages between more than one pair of attachment ends of the electrodes. In different embodiments, the voltage measuring circuit may include an amplifier to amplify the detected voltage signal. The voltage measuring circuit may also include a filter to improve the signal to noise ratio of the detected voltage signal. In preferred embodiments, the voltage measuring circuit detects and flags an open circuit and/or a short circuit.

The system of the present invention preferably includes a transmitting circuit for transmitting the detected voltage signal to a receiver through a wireless communication system. In different embodiments, the transmitting circuit may function to transmit an error indicator instead of a voltage value in response to an open circuit, a short circuit and/or an error detected by the error detecting circuit. In addition, the transmitting circuit may transmit an indicator of a signal to noise ratio with the detected voltage signal. The transmitting circuit may be in an integrated unit attached to a subject or incorporated into the electrode structure itself, for instance in electrodes implemented as Radio Frequency Identification ("RFID") circuits, which typically can be addressed individually or their transmissions individually identified. The wireless communication can be via infrared communication system, RF communication, RFID technology, or other methods. See, e.g. motes with limited processing capability described at http://www.computerworld.com/mobiletopics/mobile/story/0,10801,79572,00.html as printed on May 24, 2006 (and provided in a separate information disclosure) that may be modified in accordance with the disclosed invention to provide some or all of the described functions.

To implement wireless communication, infrared communications or radio frequency tags preferably operates to communicate bi-directionally with a controller to allow for up-loading and down-loading information to the ECG as explained in more detail below. The infrared communications may be implemented using off-the-shelf infrared communications components and preferably using a standardized communications protocol such as according to the Infrared Data Association (IrDA). IrDA is an industry-based group of over 150 companies that have developed communication standards especially suited for low cost, short range, cross-platform point-to-point communications at a wide range of speeds using infrared technology. These wireless communications standards have been adapted particularly well in mobile computing environments such as laptops and palmtops as well as peripherals such as printers to allow for ready transfer of information.

Radio frequency ("RF") communications may be readily substituted for the infrared communications to operate in a substantially similar manner in order to implement wireless communications. The RF communications may be readily implemented using commercially available, off the shelf components that employ standardized communications protocols at the network and link levels, for instance that are compliant with IEEE 802.15.4 standard. Further, wireless transceivers that operate in the 900 MHz radio band and employ a TCP/IP network communications protocol to implement a wireless Ethernet local area network (LAN) may be used to realize the benefits of the present invention.

The ECG signal can also be transmitted using RFID technology, where signals from one or more RFID tags are wirelessly transmitted to one or more receivers in a patient monitoring system. Each RFID tag may possess its own code, so that signals from more than one RFIDs would automatically be multiplexed at the patient monitor system. Preferably the RFID tags are capable of being polled by an external receiver sending a signal (which may also provide limited power) containing a specific identifier for a particular tag. Preferably, in response to recognizing the identifier, the addressed RFID tag transmits the requested information.

Motes, also known as smart dust, are tiny devices that include processing power, sensor(s) and a transceiver. Mote dimensions can be smaller than 2-3 mm. A challenge in designing motes is the integration of the sensor functionality while keeping the dimensions small and the power consumption low. The cost of motes is also rapidly coming down.

For monitoring ECG like signals, a preferred embodiment utilizes motes embedded into a band or wrap that can be attached to a patient, e.g., using Velcro to provide the required tension. Preferably, the motes are significantly simplified because in many embodiments there is little need for extensive processing or networking with other motes. Some electrode bearing band designs are described in the US Patent Publication Nos. 2005/0119701 and 2006/0084880. In addition to the electrodes disclosed in these references, with some modifications to conform to the invention disclosed herein, electrodes may traverse the surface of the wrap and may be attached at their other end to a socket in a mote to allow the mote to sense a surface voltage or current. Alternatively, the electrode assembly itself includes processing functionality in being integrated into a mote. Preferably, the mote includes signal amplification capability to enhance the voltage/current signal prior to digitizing it and then transmitting it. The transmission from a mote is, preferably, in response to a poll signal from an external signal. However, transmissions to announce the presence of the mote or the collection of motes allow monitoring devices to detect the presence of a subject.

The motes may be thought of as voltage/current sensors linked to an RFID unit. The RFID tags may be battery powered. Alternatively, the RFID technology could be developed for passive telemetry, involving radio reception of ID codes from RFID tags that are not running on battery power. The RFID tags may be powered by the heat from the patient's body or by storing energy from received radio probes or by capturing energy by sensing vibrations. Further, when a battery is utilized, in view of the extremely low power requirements of motes, a single battery could suffice the various motes attached to a surface. This may be implemented in any of the many known ways, such as embedding wires in the wrap or band to provide connectivity to the battery and a common ground while maintaining insulation from the subject. Thus, each mote is attached to the surface such that it also contacts embedded wires.

At any given time, only a few of the motes attached to a surface will be used to collect voltage/current signals. The choice of the motes to be used depends on the quality of the signal received and the need to reconstruct ECG signals in a desired format from the many motes distributed and in contact with the patients surface. Further, such a monitoring system is suitable to track a subject's data round the clock without requiring confinement of the patient to a hospital. The data can be stored and processing in a separate device for subsequent evaluation or for triggering alarm states, for instance, in response to detecting abnormal cardiac rhythms.

Passive telemetry utilizes the short-circuiting of an antenna in the RFID tag to transmit a signal. If a signal is emitted from a base station at the particular frequency that the LC circuit (comprising a coil and capacitor) of the RFID tag is tuned to, then the LC circuit would resonate with that frequency (e.g., 125 KHz, even though other frequencies are also possible in RFID chips). However, if the capacitor/antenna is short-circuited with a simple transistor for a few cycles, the emitter receives signal of a different back-scattered intensity from the RFID antenna and so is able to distinguish bits of data received. RFID passive telemetry generally has a short range of only a few centimeters, depending on the power of the transmitter and a two (receiver/transmitter) antennas design. In addition, since passive telemetry (RFID) systems convert RF energy to DC voltage, it can then charge a capacitor for powering internal circuits. For example, a few hundreds of microamperes at 3V may be taken from this system, which could power a microcontroller and associated circuits.

In a RFID based system, a plurality of voltage measurements are made available to a receiver. The receiver preferably can address particular RFID tags to elicit a response from the addressed tag. Initially, the receiver determines a set of RFID tags selected from a plurality of RFID tags that result in the best synthesized ECG signal. In the event one or more RFID tags in the set fail, for instance due to a lead coming off or other malfunctions, the receiver selects substitute RFID tags.

In another aspect, the RFID tags may be incorporated in one or more bands or belts or garments that may be worn by a patient. The tags may then be queried and an ECG signal reconstructed to provide continuous monitoring without requiring cumbersome wires to tether the patient or limit the movements of the patient. Such a belt/band/garment may include a plurality of gel based contacts that may be affixed to the patient's skin to allow continuous monitoring of the detected voltages and adjustment in the number and specific electrodes being used to synthesize the ECG signals.

A limitation of such an arrangement is that some of the gel based contacts are inevitably disrupted. As is described herein, this difficulty is overcome by the preferred embodiments by both monitoring for disruptions and implementing corrective measures to allow continuous or quasi-continuous monitoring.

Figure 6:
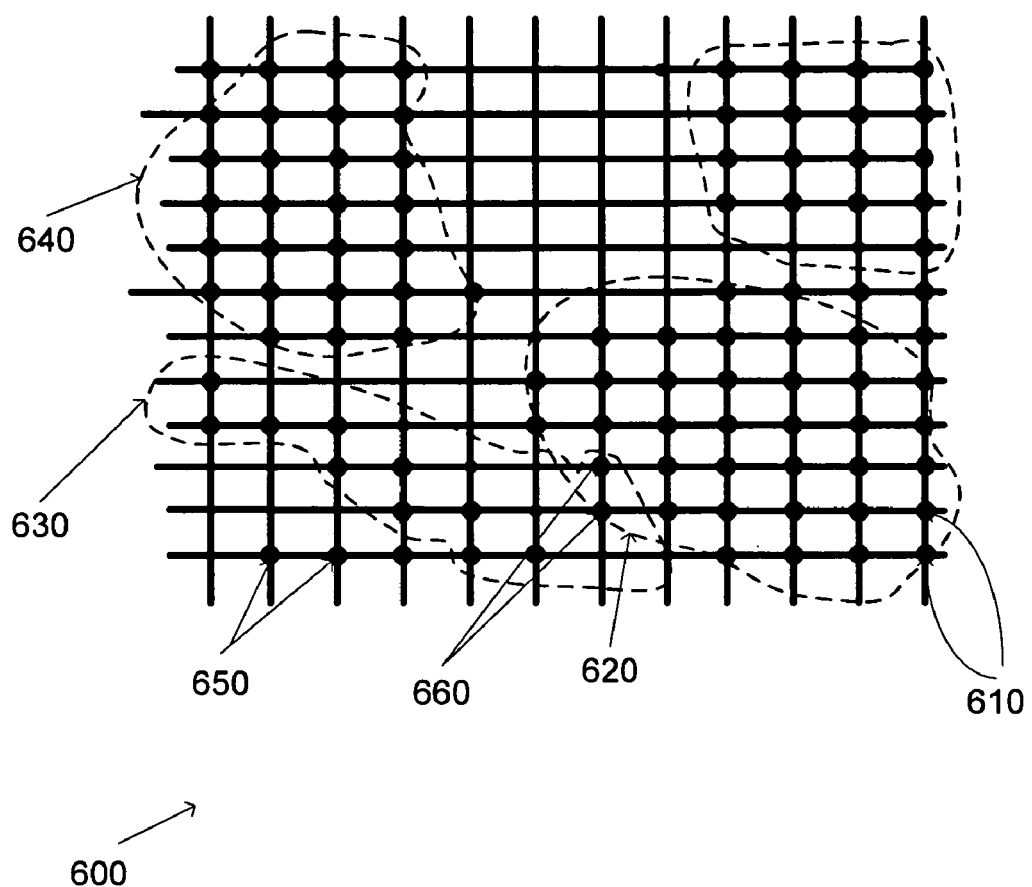
FIG. 6 shows a schematic layout of electrodes on a grid with some possible neighborhoods or collections of electrodes marked. Each electrode may be in electrical communication with one or more motes.

FIG. 6 shows one such arrangement of a plurality of electrodes arranged in a grid with RFID tags incorporated or attached to several locations. Multiple tags in the neighborhood of an electrode, for instance of an electrode shown in FIG. 2, may provide, in a preferred embodiment, candidate electrodes for deducing an ECG signal.

In FIG. 6, many electrodes are in illustrative clusters 620-640. However, there is no requirement that a regular grid should be used or that all electrodes be so clustered. The grid represents a possible support, e.g., a fabric to which or into which electrodes are attached. As seen in FIG. 6, electrodes 650 are not necessarily identified as belonging to any particular cluster. Further, some electrodes, such as electrodes 660 may belong to two or more clusters, for instance clusters 620 and 630. This permits a more flexible selection of suitable electrodes while removing stringent preconditions for manufacturing the support with the electrodes.

Figure 7:
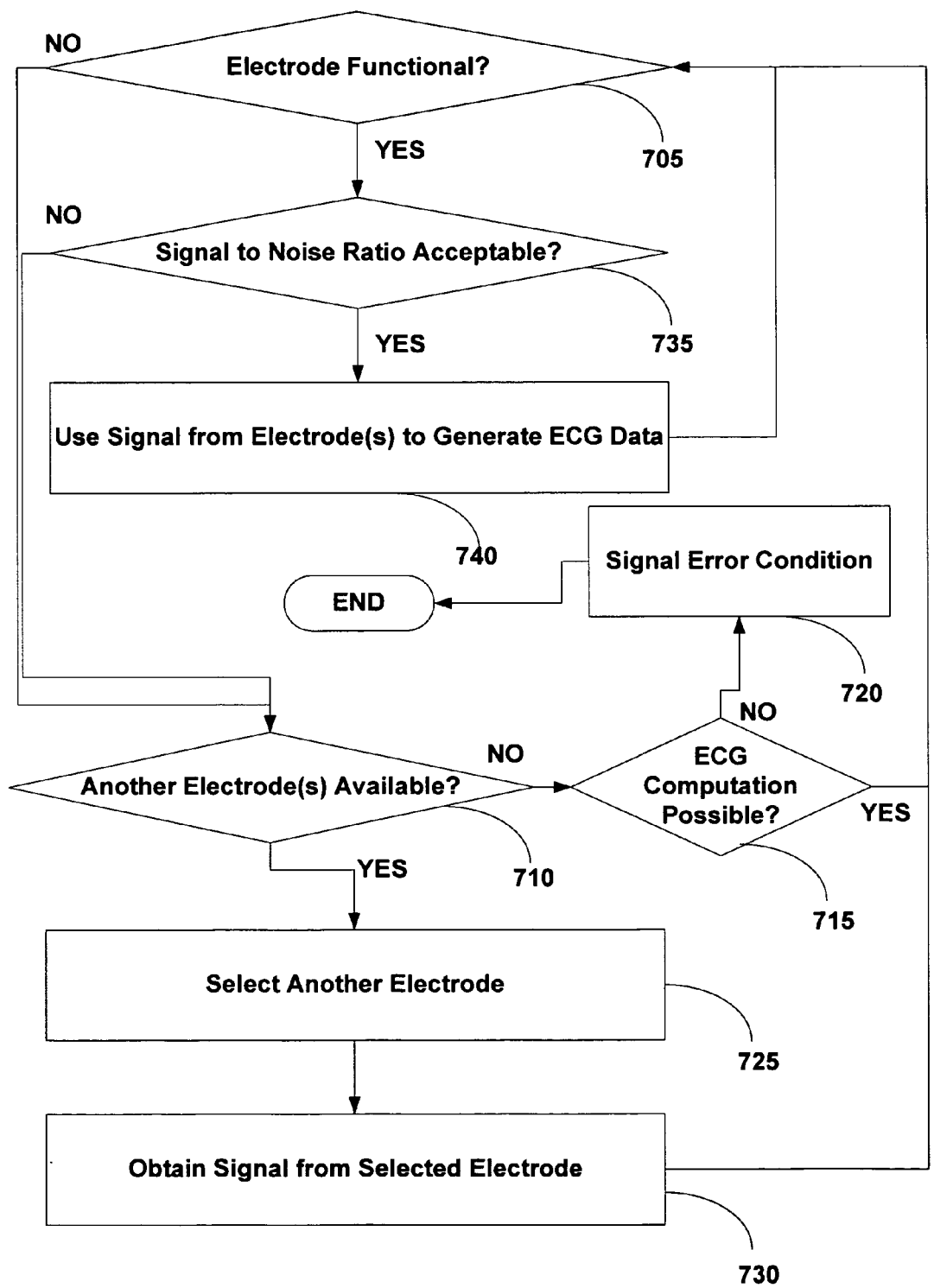
FIG. 7 is an illustrative flowchart showing introduction of an additional electrode into the set of electrodes from the available electrodes for computation of electrocardiogram signals.
Figure 8:
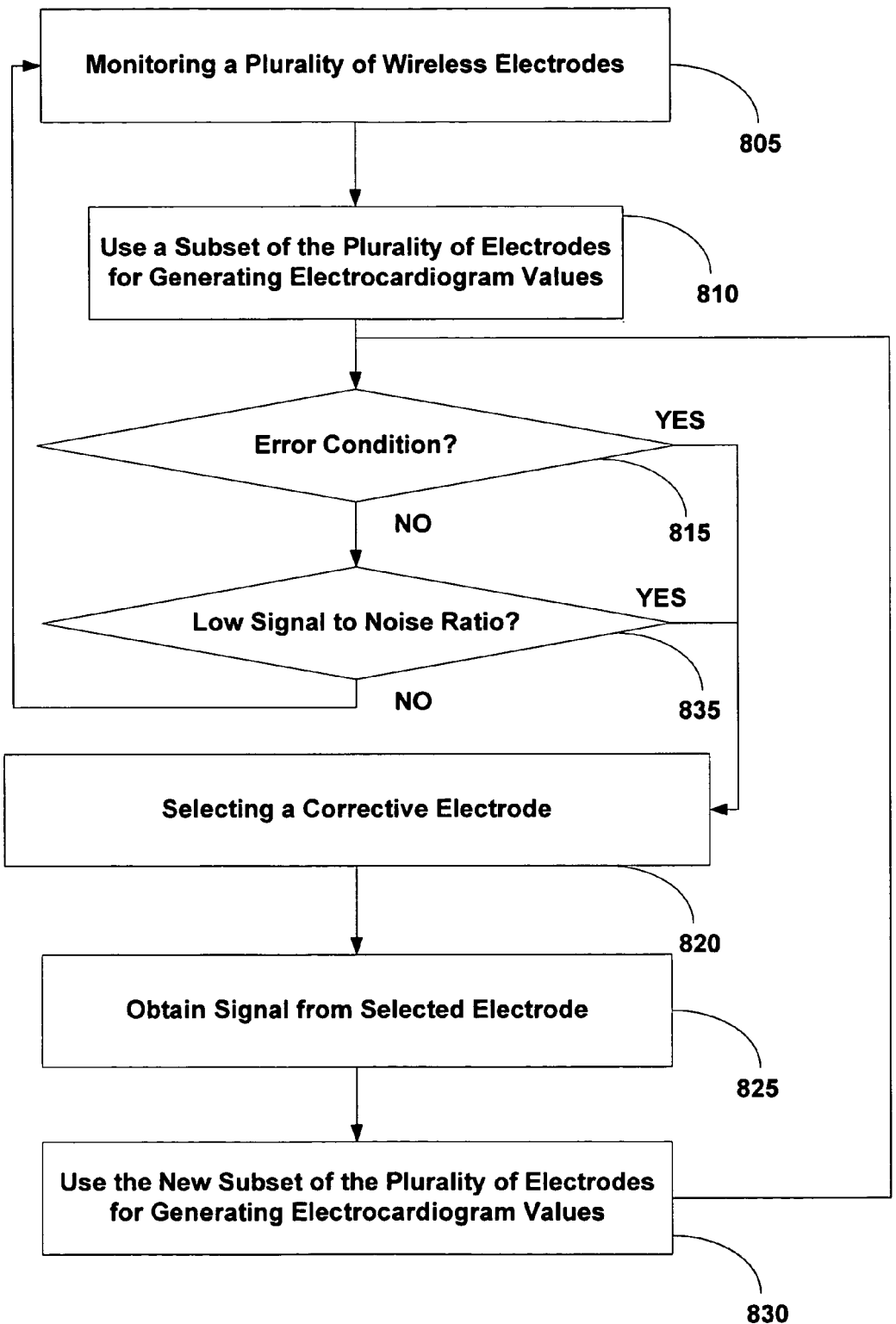
FIG. 8 is an illustrative flowchart showing use of a new subset of electrodes for computation of electrocardiogram signals.

FIGS. 7 and 8 describe methods implementable by hardware and other structure to carry out the described functions. It is preferred that many of the steps be implemented with the aid of software instructions, including those executed by one or more processors and associated operating systems and support software. However, it should be understood that the use of switches and means for accepting manual input, e.g., touch screens, keyboards, pointing devices, tablets and the like is expected and understood to be customary in applications of this type. The signal-to-noise ratio may be computed by comparison with a stored or reference signal or from the unexpected excessive variation of the signal. Therefore, it must be understood that each of the blocks and illustrative features in the Figures also invoke the structures for implementing the described steps or providing the structure FIG. 7 illustrates an illustrative method in a preferred embodiment. At step 705, a determination is made whether an electrode is functional. This may reflect detection of a short circuit, lack of response to a polling query, an open circuit or abnormal values. If an electrode is not functional, control flows to step 710 where availability of another electrode is checked. If no further electrodes are available then if it is determined that an electrocardiogram signal cannot be computed during step 715, a signal error condition is detected and flagged at step 720, e.g., by an alarm indicating that the device has largely failed and may not be able to compute a reliable electrocardiogram signal and the method terminates. If an electrocardiogram can be computed nevertheless, then control goes back to step 705 or step 735.

However, during step 710 if another electrode is available, then control passes to step 725 for selection of another electrode. The electrode may be selected after screening several electrodes or from an ordered list or algebraic ordering of electrodes or even at random including from the neighborhood of the failed electrode. During step 730 a signal fro the selected electrode(s) is acquired. The acquisition of a signal may be by polling or addressing an electrode or as a result of continuous transmissions from the electrodes. Electrodes or collections thereof may be designed to transmit upon detection of conditions suitable for transmission to reduce collisions.

During step 705 if the electrode is functional, control flows to step 735 to check the signal-to-noise ratio. If the signal-to-noise ratio is not high then control flows to step 710 as described earlier. On the other hand, with an acceptable signal-to-noise ratio, an electrocardiogram data is generated in the desired format (12-lead or some other format) during step 740 with control flowing to step 705. In alternative preferred embodiments the method may terminate.

Thus, if an electrode malfunctions, then anther electrode in the neighborhood can takeover the task of providing a suitable voltage/current signal.

FIG. 8 further illustrates the operations in accordance with a preferred embodiment. During step 805, preferably a controller, although not necessarily on a subject being monitored, monitors a plurality of electrodes. During step 810 a subset of these electrodes are used to deduce electrocardiogram data in the desired format. Control flows to step 815, during which if an error condition is detected control flows to step 820 for selection of a corrective electrode. A corrective electrode may be understood to be combinable with a subset of electrodes or be suitable for replacing one of the subset of the electrodes. During step 825 a signal is obtained from the corrective electrode, for instance by polling it, or addressing it or permitting it to transmit or merely waiting for its signal. The subset of electrodes including the corrective electrode is used to compute electrocardiogram data during step 830 with control flowing beck to decision block 815.

During step 810, if no error condition is detected, control flows to decision block 835 for evaluation of the signal-to-noise ratio in this illustrative method. If the signal-to-noise ratio is acceptable, control flows back to step 805. Otherwise, control flows to step 820.

Figure 9A:
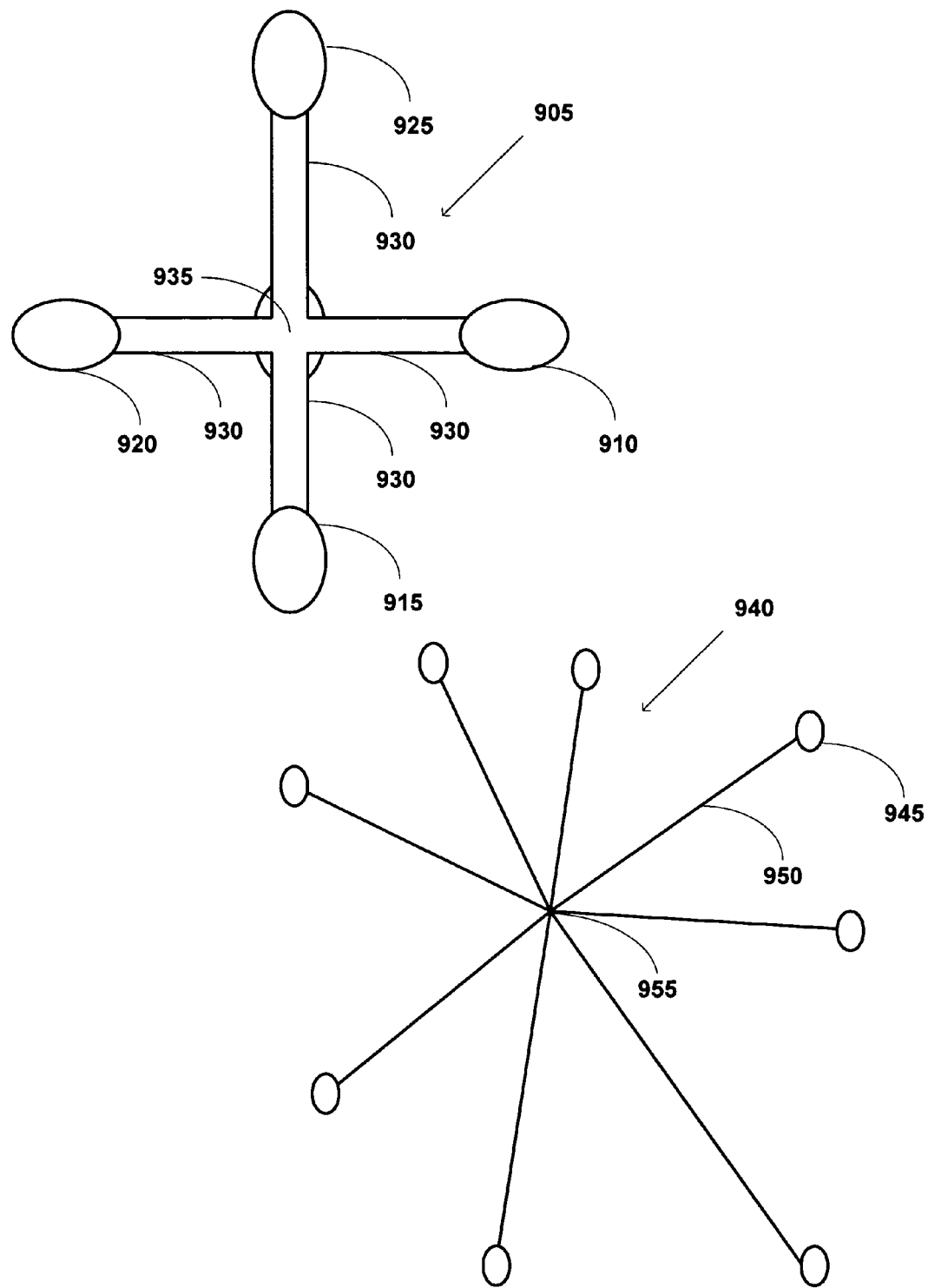
FIGS. 9A and 9B illustrates some electrode implementations suitable for the invention.
Figure 9B:
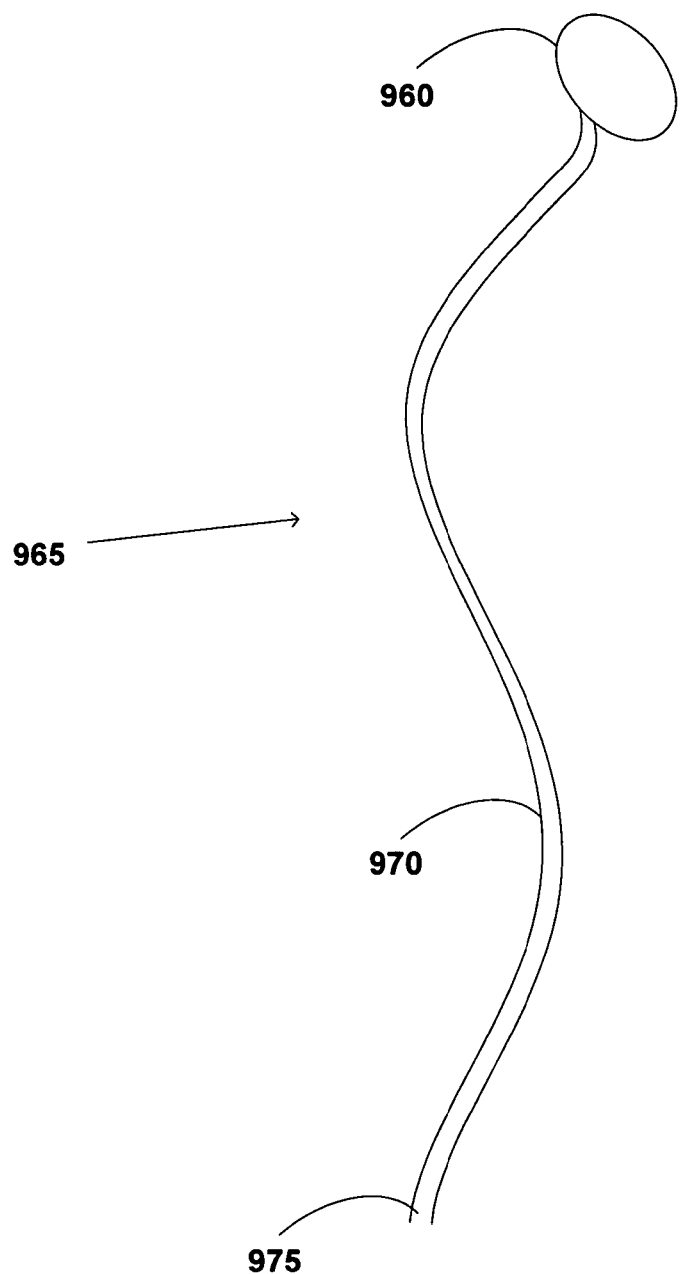

FIGS. 9A and 9B show some illustrative details of electrodes suitable for some preferred embodiments. FIG. 9A shows an illustrative electrode 905 with four contact points and one reference point arranged in a cross-like configuration. Adhesive Sensor Pads 910, 915, 920, and 925 are capable of being attached to a patient's body to sense a voltage signal relative to the reference contact 935 to which the Adhesive Sensor Pads 910-925 are connected via one or more of Arm 930. Preferably, Arms 930 are flexible. Arm 930 or an Adhesive Sensor Pad may include separately or in combination an RFID circuit to send data corresponding to the sensed voltage to a controller or receiver, preferably directly over a wireless link. To this end the circuit includes a transmission circuit. An illustrative variation on this design is presented as Electrode 940 with Pads 945, Conducting Arms 950 and a Reference 955. It should be noted that with no loss of generality the conducting arms may be integrated into a supporting fabric.

FIG. 9B shows illustrative single electrode 965 with patient end 960 suitable for attachment to a patient, while a conducting ribbon 970 connects patient end 960 to a Reference end 975, which may be attached to the ground, for instance via the patient bed or a common potential point on the body. In effect, the use of a common potential removes the contributions due to the lack of a common ground. Instead, each electrode transmits a signal corresponding to a voltage difference such that a common ground be constructed for processing the transmissions to generate ECG data.

Figure 10:
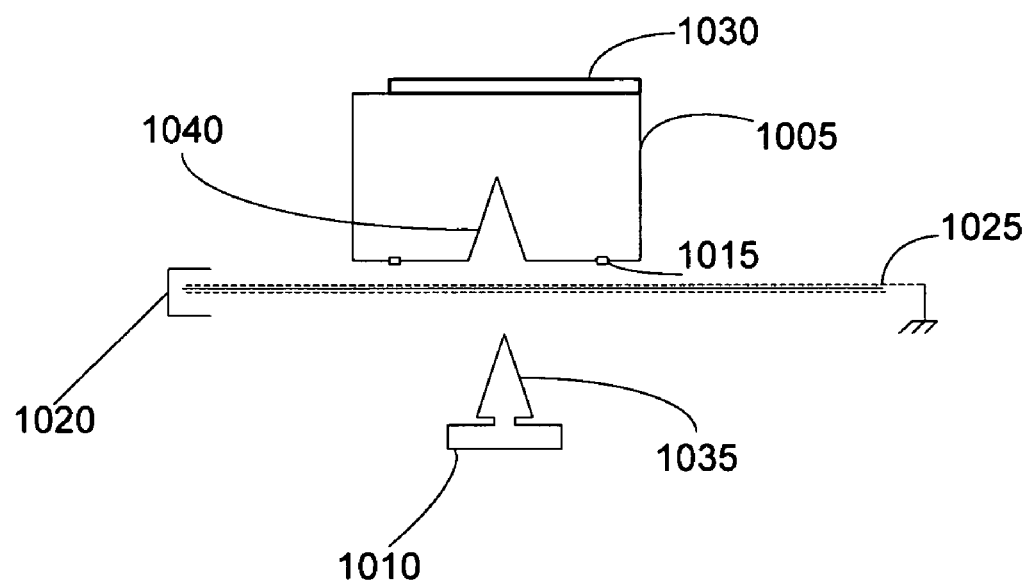
FIG. 10 illustrates a mote couplable to an electrode through a fabric or film.
Figure 11:
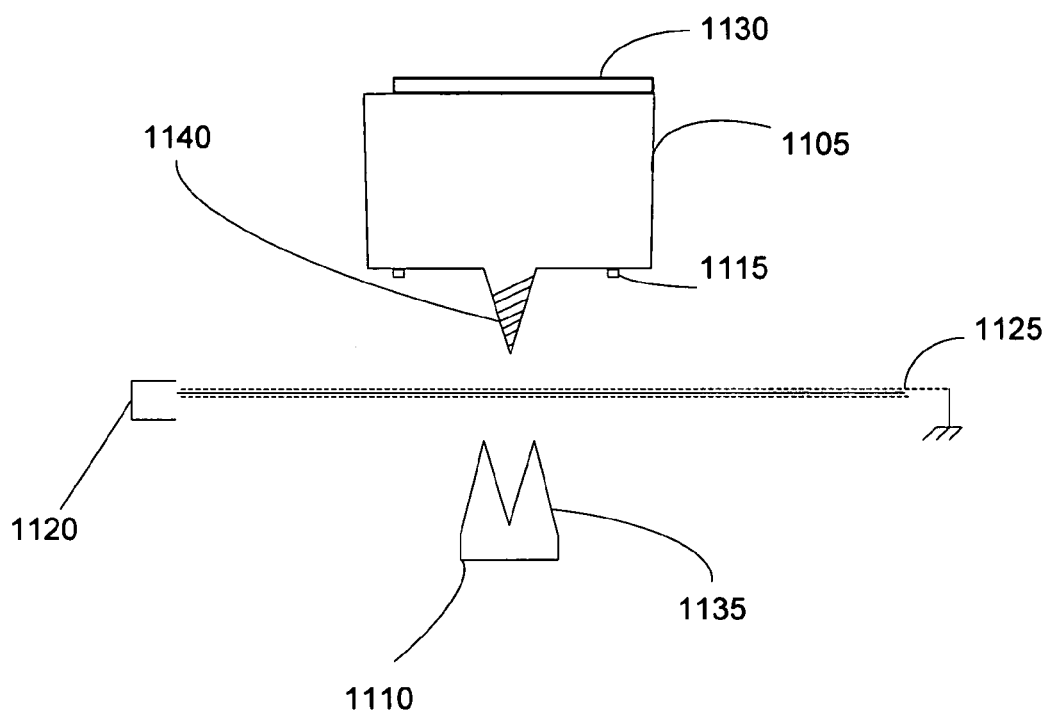
FIG. 11 illustrates alternative arrangements of motes and electrodes on a support fabric or film.

In addition, preferably there is a receiver circuit for receiving commands and/or for being polled. FIG. 10 shows a possible arrangement that incorporates a mote that may be attached to a carrier fabric or film through which it contacts an electrode. As shown, in this illustrative embodiment, mote 1005 may be connected to electrode assembly 1010 through fabric 1020. Fabric 1020 preferably incorporates on one side conducting material 1025 to provide a common ground connected to the mote via one or more contacts 1015. Mote 1005 also has a power source 1030. Electrode assembly 1010 may be in one piece or comprise many parts to provide contact 1035 to electrically and mechanically engage with complimentary site 1040 in mote 1005, including by interlocking couplings, including via screws, or customized couplings reducing assembly errors, pin connections and the like. Another embodiment with a screwed on electrode is illustrated in FIG. 11 with similar numbering as in FIG. 10 for the various illustrated features. Further, motes may be disposed on a supporting surface as shown in illustrative FIG. 6 and may even be disposed in various decorative patterns, in addition to that shown.

It should be noted that the description in FIG. 10 is not intended to be limiting as, for instance, many details are readily modified or dispensed with in alternative embodiments. As an example, power source 1030 may be shared by many motes, or they may be passive, or the power source may be a solar panel, a battery, vibration sensor, a thermocouple and the like. Further, mote 1005 may provide amplification and basic processing of the voltage detected via electrode assembly 1010. Alternatively, it may provide networking and coordination with other motes to better collect and send data, and detect errors. Furthermore, mote 1005 and electrode assembly 1010 need not sandwich a fabric in all embodiments. Indeed, in some alternative embodiments, electrode assembly 1010, partially or completely, may be integrated into mote 1005. Similarly, while a common ground is desirable, it is not required in all embodiments, as is the case if surface currents rather than voltages are being monitored.

It is preferred that mote 1005 be addressable, for instance for diagnostics or data collection. To this end, it may have a unique or relatively unique identifier. Mote 1005 may also include additional functionality, such as encryption for secure data transmission. Private-public key encryption is one way of providing security without requiring extensive processing.

Thus, continuous monitoring of a subject is possible while allowing the subject to move around while the various electrodes are pressed into service or removed from the set of electrodes used to compute the electrocardiogram data. The electrodes may be incorporated into a support, band, or garment or be attached to a subject directly. Further, networking of several monitoring stations allows a subject to move around while allowing for unobtrusive monitoring. In a preferred embodiment, the transmissions to and from are preferably encoded to provide a desired level of privacy without endangering the well-being of a subject.

In yet another aspect, the bandwidth required for transmitting the measured voltage signals is reduced in a preferred embodiment by employing a filter. The filter preferably is a dynamic filter such that filter parameters are calculated periodically based on previous time points to predict the voltage signals in the future. Further, in an analysis-by-synthesis procedure, a difference between the actual measured voltage signal and the predicted voltage signal is generated as a measure of the noise in the measured voltage signal. With effective prediction, that is, effective filters, the noise component should be Gaussian or quasi-Gaussian in form. In another aspect, the filter parameters and an indicator of the noise are transmitted for reconstruction of the measured voltage signal. However, it should be noted that in many embodiments, only the filter parameters may be transmitted with the noise component indicated by its average value. This technique allows a reduction in the bandwidth required to transmit the voltage signal by reducing transmission of redundant information in the voltage signal.

In an preferred embodiment, the transmitting circuit transmits an error indicator instead of a voltage value in response to one or more of an open circuit, a short circuit, and an error detected by the error detecting circuit. In an preferred embodiment, the transmitting circuit transmits an indicator of a signal-to-noise ratio with the detected voltage signal. This may be in form of the average energy content of a noise signal or a gain required to normalize the amplitude of the noise component to a present value or even the mean and standard deviation for the noise signal.

Therefore, a preferred embodiment indicates the signal-to-noise ratio by parameters corresponding to an error between a predicted voltage signal and a measured voltage signal (it should be also noted that the original signal may be an average signal from more than one electrode) such that the predicted voltage signal is determined from filter parameters based on a set of previously detected voltage levels. This technique allows the wireless transmissions to require little bandwidth when processing is possible at the sending end, typically with powered electrodes that include processing. In a preferred embodiment, a decision may be made to operate at more than one level of accuracy in view of the available power and other factors. For instance, for ordinary monitoring, the filter parameters with a crude measure of the noise component may suffice. However for detailed monitoring, it may be preferable to actually attempt to reconstruct the detected voltage signals at an external receiver. This requires representing the error signal in a compact form for transmission along with the filter parameters.

Thus, in another aspect, a codebook, preferably an algebraic codebook may be used to send information about the error/noise signal. This degree of complexity requires significant computation as the codebook is searched to determine a suitable set of parameters, such as an index corresponding to the error signal. The parameters are used at the receiver to retrieve from the codebook the corresponding noise signal and in conjunction with the filter parameters, allow reconstruction of the original signal. Algebraic codebooks are preferable because they do not impose the onerous storage requirements for storing the codebook.

The transmitted measure of the error signal then serves to allow accurate reconstruction of the voltage signal and/or to indicate if an electrode or set of electrodes is malfunctioning, and thus needs to be replaced by another electrode. This flexibility makes the disclosed apparatus and method for wireless cardiographic monitoring disclosed herein both robust and flexible.

Although the preceding description of the invention is in the context of the embodiments described herein, this is not intended to be a limitation on the scope of the invention. The disclosed invention encompasses the disclosed embodiments along with other embodiments having many different configurations for providing wireless communications between electrodes and patient monitoring systems. Such systems may include monitoring of temperature, or hemodynamic parameters as sensors for monitoring such parameters are perfected for integration into mote-like devices. Some descriptions of suitable sensors are found in U.S. Pat. Nos. 6,976,965 and 7,017,404.

Further, the motes may be configured to network with each other in other embodiments to allow for additional processing that takes into account data collected at more than one mote. It should be emphasized that although illustrative embodiments have been described herein in detail, that the description and drawings have been provided for purposes of illustration only and other variations both in form and detail can be added thereupon as is well understood by one having ordinary skill in the art without departing from the spirit and scope of the invention. The terms and expressions herein have been used as terms of description and not as terms of limitation or to exclude any equivalents of features shown and described or portions thereof. Further, all references cited in this disclosure, including those that are prior art, are incorporated herein by reference.

I claim:

1. An apparatus for recording potentials on a body surface comprising:
   a plurality of wireless electrodes, each electrode capable of transmitting one or more of a measured voltage or an electrode status over a relatively unique wireless link;
   a receiver configured to receive over the wireless link one or more of the measured voltage and/or status transmitted by the respective electrodes;
   wherein two or more of the plurality of electrodes belong to at least one cluster, are physically disconnected, and are in wireless communication with each other; and
   the receiver is further configured to determine whether a first electrode in the at least one cluster is functioning properly and, if the first electrode is not functioning properly, receiving a signal from the first electrode that is indicative of a status of the first electrode and selecting a second electrode in the cluster that is functioning properly to replace the first electrode.

2. The apparatus of claim 1, wherein the electrode status comprises one or more of a short circuit, a lack of response to a polling query, or an abnormal value.

3. The apparatus of claim 1, wherein the receiver is further capable of determining the respective signal-to-noise ratios of the electrodes.

4. The apparatus of claim 1, wherein one or more electrodes each comprise
   a transmitting circuit;
   an error detecting circuit; and
   a voltage measuring circuit.

5. The apparatus of claim 4, wherein the voltage measuring circuit comprises an amplifier to amplify the measured voltage.

6. The apparatus of claim 4, wherein the voltage measuring circuit comprises a filter to improve the signal-to-noise ratio of the measured voltage.

7. The apparatus of claim 1, wherein the electrodes transmit one or more of a sensed voltage signal, a plurality of parameters corresponding to the voltage signal, or an error signal.

8. The apparatus of claim 7, wherein the plurality of parameters correspond to an expected signal and the error signal is generated by comparing the difference between the expected signal and the sensed voltage signal.

9. The apparatus of claim 1, further comprising a power supply having one or more of a battery and a transducer for providing electrical potential.

10. The apparatus of claim 1, wherein the one or more electrodes each further comprise an RFID tag.

11. The apparatus of claim 1, wherein the receiver is further capable of generating ECG signals.

12. The apparatus of claim 1, wherein the plurality of electrodes are housed in an elastic band.

13. The apparatus of claim 12, wherein the elastic band comprises a common ground.

14. The apparatus of claim 1, wherein the plurality of electrodes comprise a plurality of uniquely identifiable motes.

15. A method for recording potentials on a body surface comprising:
   receiving over a wireless link a measured voltage and/or electrode status transmitted by a first wireless electrode from a plurality of wireless electrodes, wherein two or more of the electrodes, including the first electrode, belong to a first cluster, are in wireless communication with each other, and each of the two or more electrodes are physically disconnected from each other; and determining whether the first electrode in the at least one cluster is functioning properly by receiving a unique signal from the first electrode that is indicative of a status of the first electrode and, if the first electrode is not functioning properly, selecting a second electrode in the first cluster that is functioning properly to replace the first electrode.

16. The method of claim 15, wherein the plurality of electrodes comprise a plurality of uniquely identifiable motes.

17. The method of claim 15, further comprising determining the respective signal-to-noise ratios of the electrodes.

18. The method of claim 15, further comprising transmitting one or more of a sensed voltage signal from one of the plurality of wireless electrodes, a plurality of parameters corresponding to the voltage signal, or an error signal.

19. The method of claim 18, wherein the plurality of parameters correspond to an expected signal and the error signal is generated by comparing the difference between the expected signal and the sensed voltage signal.

20. An apparatus for collecting Electro-Cardiography Data comprising:

a plurality of uniquely identifiable motes that are physically disconnected and in wireless communication with each other wherein each mote comprises a wireless electrode, and, is capable of transmitting one or more of a measured voltage or a mote status over a relatively unique wireless link;

a receiver configured to receive over the wireless link one or more of the measured voltage and/or mote status transmitted by the respective motes, wherein two or more of the motes are arranged in at least one cluster; and the receiver is configured to determine whether a first mote in the at least one cluster is functioning properly by receiving a signal from the first electrode which is indicative that the first electrode is disconnected, and, if that mote is not functioning properly, selecting a second mote in the at least one cluster that is functioning properly to replace the first mote.

21. The apparatus of claim 20, wherein one or more motes each comprise a transmitting circuit;

an error detecting circuit; and a voltage measuring circuit.

22. The apparatus of claim 20, wherein the voltage measuring circuit comprises an amplifier to amplify the measured voltage.

23. The apparatus of claim 20 wherein the electrodes monitor and transmit hemodynamic parameters.

* * * * *